United States Patent [19]
Grams et al.

[11] Patent Number: 5,919,169
[45] Date of Patent: Jul. 6, 1999

[54] CANNULA LOCK AND SEAL MECHANISM

[76] Inventors: Guenter Grams, 2443 Norse Ave.;
Beven Grams, 2435 Norse Ave., both of Costa Mesa, Calif. 92627

[21] Appl. No.: 08/880,262

[22] Filed: Jun. 23, 1997

[51] Int. Cl.$^6$ ...................................................... A61M 5/00
[52] U.S. Cl. ............................ 604/241; 604/240; 604/533
[58] Field of Search .................................... 604/240, 241, 604/283, 242, 236, 238, 533, 535, 243

[56] References Cited

U.S. PATENT DOCUMENTS

| | | | |
|---|---|---|---|
| 1,668,315 | 5/1928 | Hein | 604/241 |
| 3,402,713 | 9/1968 | Senkowski et al. | 604/241 |
| 3,542,024 | 11/1970 | Burke | 604/241 |
| 5,002,538 | 3/1991 | Johnson. | |
| 5,385,555 | 1/1995 | Hausser. | |
| 5,419,775 | 5/1995 | Haffner et al.. | |
| 5,433,711 | 7/1995 | Balaban et al.. | |
| 5,456,675 | 10/1995 | Wolbring et al.. | |

*Primary Examiner*—Ronald Stright, Jr.
*Assistant Examiner*—A. T. Nguyen
*Attorney, Agent, or Firm*—Price Gess & Ubell

[57] ABSTRACT

An attachment is described whereby a cannula or needle can be connected to a syringe or vacuum-creating machine in a quick and reliable manner. The cannula attachment comprises a plug which rigidly connects to the cannula at a tip using welding or other mounting methods, such that the plug can communicate fluid into and out of the cannula. The plug includes external threads about a middle portion, and a frustro-conical nose is formed at the opposite end. The nose is sized to fit snugly into the port of the syringe or vacuum-creating device at some intermediate distance between the tip and the end of the nose. With the nose tightly in the syringe port, a channel is formed through the plug from the cannula to the syringe barrel. The attachment is held in place by a locking sleeve which receives the syringe's port and the plug within opposite ends of a longitudinal bore such that the nose projects loosely into the syringe port. Internal threads at a first end of said sleeve engage the external threads of the plug as the plug is rotated, and the engagement of the threads draw the plug increasingly farther into the locking sleeve. When the plug is substantially rotated into the locking sleeve, the nose will be lodged in the syringe port sufficiently to compress the port between the locking sleeve and the nose. An air-tight and fluid-tight seal can be achieved quickly and reliably using the above-described attachment assembly while protecting against premature decoupling due to forces transferred to the connection.

10 Claims, 1 Drawing Sheet

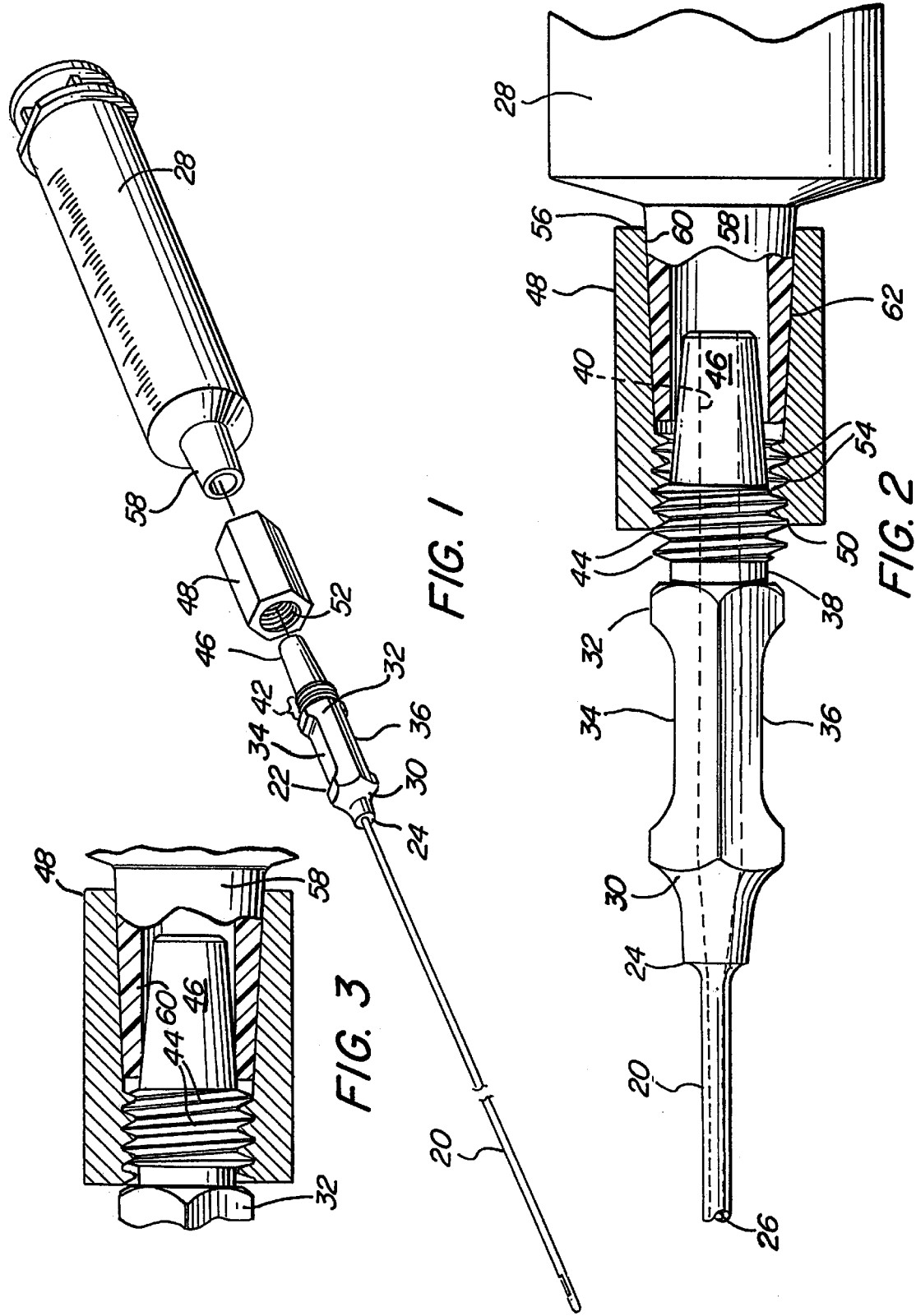

CANNULA LOCK AND SEAL MECHANISM

BACKGROUND OF THE INVENTION

1. Field of the Invention

The present invention relates to medical apparatus, and in particular to a cannula attachment which locks and seals a cannula to a mating syringe port or vacuum device quickly and reliably.

2. Description of Related Art

It is well known in the art to mount a cannula needle to a syringe for withdrawing or injecting fluids into a patient. A typical syringe comprises a cylindrical barrel which serves as a reservoir for the fluids, and a plunger which forces fluid out of the barrel or draws fluid into the barrel similar to a piston and rod assembly. In the case of fluid withdrawal or injection, a needle or cannula is connected to the syringe barrel and inserted into a patient. When withdrawing fluid from a patient, a vacuum is created in the barrel as the plunger is withdrawn, and the vacuum is transferred along a channel in the cannula to its end located at a predetermined location within the body. The fluid surrounding an opening at the end of the cannula is then drawn into the channel and into the barrel of the syringe.

A procedure which utilizes this technique is lipectomy, which involves the removal of excess fat in the layer between the epidermis and the adjacent muscle tissue. Lipectomy can be performed dry, where no fluid is initially injected into the area before the removal of the fat. However, the preferred procedure today is to use a wet technique whereby a fluid including a local anesthetic with vasoconstrictors is injected into the area, which is known to reduce postoperative pain and blood loss. In either event, a long cannula with preferably a blunt tip is used to withdraw the fat so as to limit the number of incisions in the body. The cannula is connected to either a syringe or a machine used for suction. Although for simplicity a syringe assembly is described, it is to be understood that at all times the use of a machine can be interchanged for a syringe, without deviation from the scope of the invention. The process involves manipulating the cannula back and forth, sometimes vigorously, in order to separate the fat from the attached tissue. Both the vigorous movement and the length of the cannula generate large forces which are transmitted to the connection point of the cannula with the syringe.

It is preferred to use a removable connection between the syringe and the cannula, such that the syringe can be evacuated or replaced while the cannula is in place. Various techniques have been attempted to reliably secure the cannula to the syringe which also permits quick and easy removal of the syringe from the cannula. Johnson, U.S. Pat. No. 5,002,538 discloses an adapter which is designed to mate with a syringe end such that the syringe port, shoulder, and part of the syringe barrel fit into the adapter. The adapter press-fits over the syringe using precise tolerances which purport to lock the syringe into the adapter. However, it is sometimes difficult to achieve the precise tolerances required, especially when working with plastics as is the case with most syringes. The Johnson design is also susceptible to inadvertent displacement by a withdrawing longitudinal force, which can uncouple the pressfit connection. Furthermore, the Johnson adapter covers the end of the syringe preventing a view of the withdrawn fluid until the plunger has been displaced almost a syringe diameter's distance. This is significant, because a higher blood content in the withdrawn fluid signifies that the procedure is complete, and this is determined by visually inspecting the fluid.

The prior art lacks a cannula connection which is reliable and easy to remove and install. The ideal connection would permit a clear view of the syringe barrel and secure the cannula from forces in all directions. Moreover, the connection should provide a fluid tight seal to prevent blood or other bodily fluids from leaking or escaping from the syringe.

SUMMARY OF THE INVENTION

The object and general purpose of the present invention is accomplished by a cannula attachment assembly that comprises a hollow plug which connects the cannula to the syringe, and a locking sleeve which fits over the syringe port and the plug. The plug comprises a tapered nose which is projected into the syringe's port until a seal is created. The sleeve and plug have cooperating threads which draw the plug into the sleeve as the plug is rotated until the nose fits snugly into the syringe port. Further rotation results in the slight expansion of the syringe port due to the presence of the tapered nose. With the sleeve snugly fit over the syringe port, the walls of the syringe port will become compressed between the nose of the plug and the inner surface of the sleeve, thereby creating a fluid tight seal. The connection can be easily disconnected by a counter-rotation of the plug thereby disengaging the cooperating threads.

BRIEF DESCRIPTION OF THE DRAWINGS

The exact nature of this invention, as well as all its objects and advantages, will become readily apparent upon reference to the following detailed description when considered in conjunction with the accompanying drawings, in which like reference numerals designate like components throughout the figures thereof, and wherein:

FIG. 1 is an exploded oblique view of the assembly;

FIG. 2 is a side view, partially in cut-away, of the assembly prior to complete connection; and FIG. 3 is a side view, partially in cut-away, of the assembly after complete connection.

DETAILED DESCRIPTION OF THE PREFERRED EMBODIMENTS

The following description is provided to enable any person skilled in the art to make and use the invention and sets forth the best modes contemplated by the inventor of carrying out his invention. Various modifications, however, will remain readily apparent to those skilled in the art, since the general principles of the present invention have been defined herein specifically to provide an attachment assembly for reliably connecting and sealing a cannula to a syringe port or other suction device.

A preferred embodiment of present invention is illustrated generally in FIGS. 1 through 3, which depict a cannula 20 such as those typically used in lipectomy procedures. The cannula 20 is rigidly connected to a hollow plug 22 which is preferably machined from stainless steel or the like. The plug 22 includes a tip 24 onto which the cannula 20 can be welded or otherwise fixed in a permanent or semi-permanent rigid manner to form a unitary cannula-plug construction. The connection between the cannula 20 and the plug 22 at the shoulder 30 requires that the channel 26 in the cannula 20 open into a cavity 40 in the plug 22 so that fluid can be transmitted through the attachment from the cannula 20 to a syringe 28. The plug 22 preferably includes a section of thicker construction having a hexagonal profile 32 in a preferred embodiment. The hexagonal section preferably further comprises first and second recessed regions 34,36 on opposite sides which have a length selected to accommodate a finger and thumb. The recessed regions 34,36 provide convenient locations to grasp and rotate the plug 22, the necessity of which will be described below.

The hexagonal profile 32 of the plug 22 narrows at a neck 38 which there begins a threaded region 42 having a series of threads 44 as shown in FIG. 2. The threaded region 42 connects to a smooth, tapered nose 46, preferably having a frustro-conical shape. The cavity 40 extends the length of the plug and opens at the nose 46.

A locking sleeve 48 preferably shaped like a lug or elongated nut has a longitudinal bore 52 therethrough with internal threads at a first end 50. The locking sleeve, like the cannula and plug, are preferably made of a stainless steel. Although a hexagonal profile is shown, the locking sleeve may have a round, textured surface or other shape which provides a good gripping surface. The internal threads 54 at the first end 50 are formed on the inner walls of the locking sleeve 48 and are designed to mate with the external threads 44 adjacent the nose 46. The opposite end 56 of the longitudinal bore 52 in the locking sleeve 48 is smooth and sized to fit snugly over the port 58 of syringe 28 or a port of a vacuum creating device (not shown). A close fit is desirable between the outside wall 60 of the port 58 and the inner wall 62 of the locking sleeve. That is, the locking sleeve 48 should slide almost freely on the syringe port outer wall, with some contact between the smooth portion of the locking sleeve and the outer wall of the syringe port preferable. In a preferred embodiment, the longitudinal bore of the locking sleeve 48 widens at the end 56 to better accommodate the tapered port of a typical syringe such as that used in a lipectomy.

Having described the individual elements, the interaction of the assembly will now be described. Once locking sleeve 48 is located on the port 58 as shown in FIG. 2 with the threaded first end 50 at the exit of port 58, the nose 46 of the plug 22 projects into the exit of the syringe port 58. Insertion of the plug 22 into the sleeve 48 as shown brings the internal threads 54 on the locking sleeve 48 in position to engage with the external threads 44 on the plug. If the plug 22 is then rotated, the internal threads 54 cooperate with the external threads 44 to draw the plug increasingly farther into the locking sleeve 48. As rotation of the plug 22 continues, the nose 46 projects farther into the port 58 until eventually resistance is encountered. At this point, further rotation causes the nose 46 to wedge into the exit of the port 58 thereby causing the port walls 62 to expand slightly. As rotation is continued (see FIG. 3), the wall of the port 58 is compressed between the nose 46 on the inside of port 58 and the locking sleeve 48 on the outside of port 58, creating an air-tight and fluid-tight seal.

Rotation in the opposite direction withdraws the plug from the sleeve, allowing disassembly of the apparatus.

It will be understood that the embodiment described herein are merely exemplary and that a person skilled in the art may make many variations and modifications without departing from the spirit and scope of the invention. All such variations and modifications are intended to be included within the scope of the invention as defined in the appended claims.

What is claimed is:

1. A cannula attachment for removably attaching and sealing a cannula to a syringe port, the attachment comprising:
   a plug for connection to the cannula attachment having a tapered cylindrical nose sized to fit inside the syringe port, an externally threaded section, and a longitudinal bore therethrough; and
   a sleeve having first and second ends, the first end sized to fit over the syringe port, and the second end sized to receive the plug therein, including an internally threaded section engagable with the externally threaded section of the plug;
   whereby rotation of the plug with respect to the sleeve projects the nose of the plug firmly into the syringe port, the sleeve and the cylindrical nose of the plug cooperating to form a seal with the syringe port by squeezing the port between the internal plug and the external sleeve.

2. The mechanism of claim 1 wherein the sleeve radially diverges at the first end to accommodate a tapered syringe port.

3. The cannula attachment of claim 1 wherein the plug further comprises a portion between the cannula and the external threads having recesses adapted for grasping and rotating the plug.

4. The mechanism of claim 1 wherein the plug and sleeve are stainless steel.

5. A cannula for removable attachment to a cylindrical port, the cannula comprising:
   a needle having first and second ends and a longitudinal bore therebetween;
   a hollow plug connected to the needle and in fluid communication with the longitudinal bore, the hollow plug comprising a tapered cylindrical nose at a first end sized to fit inside the cylindrical port, and a second end having external threads; and
   a sleeve sized to fit over the cylindrical port at a first end and sized to receive the plug in a second end, the second end including internal threads engagable with the external threads of the plug;
   whereby upon engagement of the external threads of the plug with the internal threads of the sleeve and upon rotation of the plug in the sleeve, the nose of the plug is projected into the cylindrical port, compressing the cylindrical port between the nose of the plug and the sleeve, thereby forming a seal.

6. The mechanism of claim 1 wherein the plug and sleeve are stainless steel.

7. The mechanism of claim 5 wherein the sleeve radially diverges at the first end to accommodate a tapered syringe port.

8. A cannula assembly for releasably locking to a syringe port, comprising:
   an elongated cannula having an opening at a distal end and a channel from the opening to a proximal end;
   a plug rigidly mounted to the elongated cannula at its proximal end, the plug including a cavity in fluid communication with the channel in the cannula, the plug having a tapered nose with a tip smaller than the inside diameter of the syringe port and a base larger than the syringe port, the plug also having external threads about a middle portion thereof; and
   a sleeve having a first end sized to receive the syringe port and a second end sized to receive the tapered nose of the plug, the second end of the sleeve having internal threads for engagement with the external threads of the plug,
   whereby the tapered nose of the plug and the sleeve form a seal with the syringe port when the external threads of the plug and the internal threads of the sleeve are operably engaged to squeeze the syringe port between them.

9. A cannula attachment and sealing assembly comprising:
- a locking sleeve including a longitudinal bore sized at a first end to securely receive a tubular port, and having internal threads at a second end; and
- a plug connected to a cannula, said plug including external threads for mating with the internal threads of said locking sleeve, said plug including a tapered nose for projecting into the tubular port when said plug is inserted into said locking sleeve, whereby the tubular port is compressed between the tapered nose of said plug and the locking sleeve when the plug is rotated with respect to the locking sleeve.

10. A cannula attachment for removably attaching and sealing a cannula to a syringe port, said attachment comprising:
- a plug connected to the cannula attachment having a tapered cylindrical nose sized to fit inside the syringe port, an externally threaded section, and a longitudinal bore thereinthrough; and
- a sleeve having first and second ends, the first end sized to fit over the syringe port, and the second end sized to receive the plug therein, including an internally threaded section engagable with the externally threaded section of the plug;
- whereby rotation of the plug results in the walls of the syringe port to become compressed between the plug and the inner surface of the sleeve.

* * * * *